US007964738B2

(12) United States Patent
Gately et al.

(10) Patent No.: US 7,964,738 B2
(45) Date of Patent: Jun. 21, 2011

(54) PHARMACEUTICAL COMPOSITIONS AND METHODS OF USE OF LIPOPHILIC, SILICON-SUBSTITUTED, CYCLOOXYGENASE-2 SELECTIVE NON-STEROIDAL ANTI-INFLAMMATORY DRUGS AND DERIVATIVES

(75) Inventors: Stephen Gately, Scottsdale, AZ (US);
Stephen P. Wanaski, Chicago, IL (US)

(73) Assignee: Silamed, Inc., Scottsdale, AZ (US)

( * ) Notice: Subject to any disclaimer, the term of this patent is extended or adjusted under 35 U.S.C. 154(b) by 1032 days.

(21) Appl. No.: 11/551,579

(22) Filed: Oct. 20, 2006

(65) Prior Publication Data

US 2007/0129331 A1    Jun. 7, 2007

Related U.S. Application Data

(63) Continuation-in-part of application No. PCT/US2005/013233, filed on Apr. 19, 2005.

(60) Provisional application No. 60/563,673, filed on Apr. 20, 2004.

(51) Int. Cl.
*C07F 7/02* (2006.01)
*A61K 31/695* (2006.01)
*C07D 231/00* (2006.01)

(52) U.S. Cl. .......................... 548/406; 514/63; 548/110

(58) Field of Classification Search .................... 514/63; 548/110, 406
See application file for complete search history.

(56) References Cited

U.S. PATENT DOCUMENTS

| 3,285,908 A | 11/1966 | Shen |
| 3,336,194 A | 8/1967 | Shen |
| 5,436,265 A | 7/1995 | Black et al. |
| 5,510,368 A | 4/1996 | Lau et al. |
| 5,607,966 A | 3/1997 | Hellberg et al. |
| 5,681,964 A | 10/1997 | Ashton et al. |
| 5,811,438 A | 9/1998 | Hellberg et al. |
| 6,399,647 B2 | 6/2002 | Kalgutkar et al. |
| 2002/0160988 A1 | 10/2002 | Amitai et al. |

FOREIGN PATENT DOCUMENTS

WO      WO 96/01830      1/1996

OTHER PUBLICATIONS

International Search Report and written opinion from corresponding PCT Application No. PCT/US2005/013233 dated Dec. 15, 2006.
J. Schwartz, Remingtons's Pharmaceutical Sciences, Part 8 "Pharmaceutical Preparations and Their Manufacture", pp. 1435-1694, 1990.
W. Black, et al. "From Indomethacin to a Selective COX-2 Inhibitor: Development of Indolalkanoic Acids as Potent and Selective Cyclooxygenase-2 Inhibitors" Bioorganic & Medical Chemistry Letters, vol. 6, No. 6, pp. 725-730 (1996).

Chan, et al. "Pharmacology of a Selective Cyclooxygenase-2 Inhibitor, L-745,337: A Novel Nonsteroidal Anti-inflammatory Agent with an Ulcerogenic Sparing.Effect in Rat and Nonhuman Primate Stomach" The Journal of Pharmacology and Experimental Therapeutics, vol. 274, No. 3, pp. 1531-1537 (1995).
Flynn, et al. "Nonsteroidal Antiinflammatory Drug Hydroxamic Acids. Dual Inhibitors of Both Cyclooxygenase and 5-Lipoxygenase" J. Med. Chem, vol. 33, No. 8, pp. 2070-2072 (1990).
Futaki, et al. "NS-398, a New Anti-inflammatory Agent, Selectively Inhibits Prostaglandin G/H Synthase/Cyclooxygenase (COX-2) Activity in Vitro" Prostaglandins, vol. 47, pp. 55-59 (1994).
Gans, et al. "Anti-Inflammatory and Safety Profile of DuP 697, a Novel Orally Effective Prostaglandin Synthesis Inhibitor" J Pharmacol Exp. Ther., vol. 254, pp. 180-187 (1990).
Kalgutkar, et al. "Aspirin-like Molecules that Covalently Inactivate Cyclooxygenase-2" Science, vol. 280, pp. 1268-1270 (May 22, 1998).
Khanna, et al. "1,2-Diarylimidazoles as Potent, Cyclooxygenase-2 Selective, and Orally Active Antiinflammatory Agents" J. Med. Chem., vol. 40, No. 11, pp. 1634-1647 (1997).
Khanna, et al. "1,2-Diarylpyrroles as Potent and Selective Inhibitors of Cyclooxygenase-2" J. Med. Chem., vol. 40, No. 11, pp. 1619-1633 (1997).
Kolasa, et al. "Nonsteroidal Anti-Inflammatory Drugs as Scaffolds for the Design of 5-Lipoxygenase Inhibitors" J. Med. Chem., vol. 40, No. 5, pp. 819-824 (1997).
Li, et al. "Cyclooxygenase-2 Inhibitors. Synthesis and Pharmacological Activities of 5-Methanesulfonamido-1-indanone Derivatives" J. Med. Chem., vol. 38, No. 25, pp. 4897-4905 (1995).
Li, et al. "1,2-Diarylcyclopentenes as Selective Cyclooxygenase-2 Inhibitors and Orally Active Anti-inflammatory Agents" J. Med. Chem., vol. 38, No. 22, pp. 4570-4578 (1995).
Li, et al. "Novel Terphenyls as Selective Cyclooxygenase-2 Inhibitors and Orally Active Anti-inflammatory Agents" J. Med. Chem., vol. 39, No. 9, pp. 1846-1856 (1996).
Luong, et al. "Flexibility of the NSAID Binding Site in the Structure of Human Cyclooxygenase-2" Nature Structural Biology, vol. 3, No. 11, pp. 927-933 (1996).
Meade, et al. "Differential Inhibition of Prostaglandin Endoperoxide Synthase (Cyclooxygenase) Isozymes by Aspirin and Other Nonsteroidal Anti-inflammatory Drugs" The Journal of Biological Chemistry, vol. 268, No. 9 pp. 6610-6614 (1993).

(Continued)

*Primary Examiner* — Shengjun Wang
(74) *Attorney, Agent, or Firm* — Robert M. Gould; Duane Morris LLP

(57) ABSTRACT

Novel compositions of silicon-substituted carboxylic acid-containing-nonsteroidal anti-inflammatory drugs, their preparation and use in methods for treating, preventing and/or reducing inflammation, pain, angiogenesis, and cortical dementias including Alzheimer's disease, inflammation-related cardiovascular disorders and cancer are described. The compositions and methods are effective at decreasing or reversing the gastrointestinal, renal and other toxicities resulting from the use of non-selective carboxylate-containing-nonsteroidal anti-inflammatory drugs.

6 Claims, No Drawings

OTHER PUBLICATIONS

Nakamura, et al. "Studies of Antiinflammatory Agents. II. Synthesis and Pharmacological Properties of 2'-(Phenylthio)methanesulfonanilides and Related Derivatives" Chem. Pharm. Bull., vol. 41, No. 5, pp. 894-906 (1993).

Tsuji, et al. "Studies of Anti-inflammatory Agents. IV. Synthesis and Pharmacological Properties of 1, 5-Diarylpyrazoles and Related Derivatives" Chem. Pharm. Bull., vol. 45, No. 6, pp. 987-995 (1997).

Penning, et al. Synthesis and Biological Evaluation of the 1, 5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celecoxib) J. Med. Chem., vol. 40, No. 9, pp. 1347-1365 (1997).

Prasit, et al. "L-745,337: A Selective Cyclooxygenase-2 Inhibitior" Medicinal Chemistry Research, vol. 5, pp. 364-374 (1995).

Reitz, et al. "Novel 1, 2-Diarylcyclopentenes are Selective, Potent, and Orally Active Cyclooxygenase Inhibitors" Medicinal Chemistry Research, vol. 5, pp. 351-363 (1995).

Remmel, et al. "Studies on the Metabolism of the Novel, Selective Cyclooxygenase-2 Inhibitor Indomethacin Phenethylamide in Rat, Mouse, and Human Liver Microsomes: Identification of Active Metabolites" Drug Metabolism and Disposition, vol. 32, No. 1, pp. 113-122 (2004).

Riendeau, et al. "Biochemical and Pharmacological Profile of a Tetrasubstituted furanone as a Highly Selective COX-2 Inhibitor" British Journal of Pharmacology, vol. 121, pp. 105-117 (1997).

Leblanc, et al. "A New Series of Selective COX-2 Inhibitors: 5, 6-Diarylthiazolo [3,2-b][1,2,4]Triazoles" Bioorganic & Medicinal Chemistry Letters, vol. 7, No. 1., pp. 57-62 (1997).

Showell, et al. "Chemistry Challenges in Lead Optimization: Silicon Isosteres in Drug Discovery" Drug Discovery Today, vol. 8, No. 12, pp. 551-556 (2003).

Tacke, et al. "Sila-substitution—A Usefult Strategy for Drug Design" Endeavour, vol. 10, No. 4, pp. 191-197 (1986).

Tanaka, et al. "Pharmacological Studies of the New Antiinflammatory Agent 3-Formylamino-7-methylsulfonylamino-6-phenoxy-4H-1-benzopyran-4-one" Arzneimittelforschung, vol. 42, No. 7, pp. 935-944, 1992.

Therien, et al. "Synthesis and Biological Evaluation of 5, 6-Diarylimidazo [2.1-b]Thiazole as Selective COX-2 Inhibitors" Bioorganic & Medicinal Chemistry Letters, vol. 7, No. 1, pp. 47-52 (1997).

Vane, et al. "Inducible Isoforms of Cyclooxygenase and Nitric-Oxide Synthase in Inflammation" Proc. Natl. Acad. Sci. USA, vol. 91, pp. 2046-2050 (1994).

Wiesenberg, et al. "The Pharmacological Profile of CGP 28238, A Novel Highly Potent Anti-Inflammatory Compound" Drugs Exptl. Clin. Res., vol. 15, pp. 501-509 (1989).

Futaki, et al. "NS-398, A Novel Non-Steroidal Anti-Inflammatory Drug with Potent Analgesic and Antipyretic Effects, Which Causes Minimal Stomach Lesions" Gen. Pharmac., vol. 24, No. 1, pp. 105-110 (1993).

Klein, et al. "Selective Inhibition of Cyclooxygenase 2" Biochemical Pharacology, vol. 48, No. 8, pp. 1605-1610 (1994).

PHARMACEUTICAL COMPOSITIONS AND METHODS OF USE OF LIPOPHILIC, SILICON-SUBSTITUTED, CYCLOOXYGENASE-2 SELECTIVE NON-STEROIDAL ANTI-INFLAMMATORY DRUGS AND DERIVATIVES

The present application claims priority from and is a continuation-in-part of PCT/US2005/13233 filed Apr. 19, 2005, which is a continuation of U.S. application Ser. No. 60/563,673 filed Apr. 20, 2004 which is now expired.

BACKGROUND OF THE INVENTION

Non-steroidal anti-inflammatory drugs (NSAIDs) are widely used because of their anti-inflammatory and analgesic activity. It is commonly recognized that NSAIDs exert their effect by blocking the activity of cyclooxygenase (COX), also known as prostaglandin G/H synthase (PGHS), the enzyme that converts arachidonic acid into prostanoids. Inhibition of the biosynthesis of prostanoids, the mediators of pain, fever, and inflammation, has long been a therapeutic target of anti-inflammatory drug discovery. The therapeutic use of conventional NSAIDs is limited by drug-associated side effects, such as severe gastric ulceration, bleeding and renal toxicity.

Two forms of COX have been identified, a constitutive isoform (COX-1), and an inducible isoform (COX-2), of which expression is upregulated at sites of inflammation (see Vane, J R; Mitchell, J A; Appleton, I; Tomlinson, A et al., Proc. Nat'l. Acad. Sci. USA, 1994, 91, 2046). COX-1 is believed to play a physiological role in gastrointestinal and renal protection, while COX-2 appears to play a predominant pathological role in inflammatory conditions. The NSAIDs currently on the market inhibit both COX-1 and COX-2 isoforms with little variation in selectivity, explaining the beneficial (inhibition of COX-2) and harmful (inhibition of COX-1) effects. The selective inhibition of COX-2 has been a goal of drug developers. It is thought that this will reduce or eliminate the GI irritation caused by COX-1 inhibition.

The differential tissue distribution of COX-1 and COX-2 provides a basis for the development of drugs that are selective COX-2 inhibitors, such that the specificity for the inhibition of COX-2 far exceeds inhibition of COX-1 (see Meade, Smith, and DeWift, J. Biol. Chem. (1993) 268:6610-6614)). Detailed structure-activity relationship studies have been reported for two general structural classes of selective COX-2 inhibitors, including certain acidic sulfonamides and diarylheterocyclics. The in vivo activities of these selective COX-2 inhibitors support the hypothesis that selective COX-2 inhibition is anti-inflammatory and non-ulcerogenic (see Gans, Galbraith, Roman, Haber, Kerr, Schmidt, Smith, Hewes, and Ackerman, "Anti-Inflammatory and Safety Profile of DuP 697, a Novel Orally Effective Prostaglandin Synthesis Inhibitor", J. Pharmcol Exp. Ther. (1990) Vol. 254, pp. 180-187; Penning, Talley, Bertenshaw, Carter, Collins, Docter, Graneto, Lee, Malecha, Miyashiro, Rogers, Rogier, Yu, Anderson, Burton, Cogburn, Gregory, Koboldt, Perkins, Seibert, Veenhuizen, Zhang, and Isakson, "Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrazol-1-yl]benzenesulfonamide (SC-58635, Celecoxib)", J. Med. Chem. (1997) Vol. 40, pp. 1347-1365; Khanna, Weier, Yu, Xu, Koszyk, Collins, Koboldt, Veenhuizen, Perkins, Casler, Masferrer, Zhang, Gregory, Seibert, and Isakson, "1,2-Diarylimidazoles as Potent Cyclooxygenase-2 Selective, and Orally Active Antiinflammatory Agents", J. Med. Chem. (1997) Vol. 40, pp. 1634-1647; Khanna, Weier, Yu, Collins, Miyashiro, Koboldt, Veenhuizen, Curie, Siebert, and Isakson, "1,2-Diarylpyrroles as Potent and Selective Inhibitors of Cyclooxygenase-2", J. Med. Chem. (1997) Vol. 40, pp. 1619-1633; Tsuji, Nakamura, Konishi, Tojo, Ochi, Senoh, and Matsuo, "Synthesis and Pharmacological Properties of 1,5-Diarylyrazoles and Related Derivatives", Chem. Pharm. Bull. (1997) Vol. 45, pp. 987-995; Riendeau, Percival, Boyce, Brideau, Charleson, Cromlish, Ethier, Evans, Falgueyret, Ford-Hutchinson, Gordon, Greig, Gresser, Guay, Kargman, Leger, Mancini, O'Neill, Quellet, Rodger, Therien, Wang, Webb, Wong, Xu, Young, Zamboni, Prasit, and Chan, "Biochemical and Pharmacological Profile of a Tetrasubstituted Furanone as a Highly Selective COX-2 Inhibitor", Br. J. Pharmacol. (1997) Vol. 121, pp. 105-117; Roy, Leblanc, Ball, Brideau, Chan, Chauret, Cromlish, Ethier, Gauthier, Gordon, Greig, Guay, Kargman, Lau, O'Neill, Silva, Therien, Van Staden, Wong, Xu, and Prasit, "A New Series of Selective COX-2 Inhibitors: 5,6-Diarylthiazolo[3,2-b][1,2,4]-triazoles", Bioorg. Med. Chem. Lett. (1997) Vol. 7, pp. 57-62; Therien, Brideau, Chan, Cromlish, Gauthier, Gordon, Greig, Kargman, Lau, Leblanc, Li, O'Neill, Riendeau, Roy, Wang, Xu, and Prasit, "Synthesis and Biological Evaluation of 5,6-Diarylimidazo[2.1-b]thiazoles as Selective COX-2 Inhibitors", Bioorg. Med. Chem. Lett. (1997) Vol. 7, pp. 47-52; Li, Norton, Reinhard, Anderson, Gregory, Isakson, Koboldt, Masferrer, Perkins, Seibert, Zhang, Zweifel, and Reitz, "Novel Terphenyls as Selective Cyclooxygenase-2 Inhibitors and Orally Active Anti-Inflammatory Agents", J. Med. Chem. (1996) Vol. 39, pp. 1846-1856; Li, Anderson, Burton, Cogburn, Collins, Garland, Gregory, Huang, Isakson, Koboldt, Logusch, Norton, Perkins, Reinhard, Seibert, Veenhuizen, Zhang, and Reitz, "1,2-Diarylcyclopentenes as Selective Cyclooxygenase-2 Inhibitors and Orally Active Anti-Inflammatory Agents", J. Med. Chem. (1995) Vol. 38, pp. 4570-4578; Reitz, Li, Norton, Reinhard, Huang, Penick, Collins, and Garland, "Novel 1,2-Diarylcyclopentenes are Selective Potent and Orally Active Cyclooxygenase Inhibitors", Med. Chem Res. (1995) Vol. 5, pp. 351-363; Futaki, Yoshikawa, Hamasaka, Arai, Higuchi, Iizuka, and Otomo, "NS-398, A Novel Nonsteroidal Antiinflammatory Drug with Potent Analgesic and Antipyretic Effects, which Causes Minimal Stomach Lesions", Gen. Phamacol. (1993) Vol. 24, pp. 105-110; Wiesenberg-Boetcher, Schweizer, Green, Muller, Maerki, and Pfeilschifter, "The Pharmacological Profile of CGP 28238, A Novel Highly Potent Anti-Inflammatory Compound", Drugs Exptl Clin Res. (1989) Vol. XV, pp. 501-509; Futaki, Takahashi, Yokoyama, Arai, Higuchi, and Otomo, "NS-398, A New Anti-Inflammatory Agent, Selectively Inhibits Prostaglandin G/H Synthase/Cyclooxygenase (COX-2) Activity in vitro", Prostaglandins (1994) Vol. 47, pp. 55-59; Klein, Nusing, Pfeilschifter, and Ullrich, "Selective Inhibition of Cyclooxygenase-2", Biochem. Pharmacol. (1994) Vol. 48, pp. 1605-1610; Li, Black, Chan, Ford-Hutchinson, Gauthier, Gordon, Guay, Kargman, Lau, Mancini, Quimet, Roy, Vickers, Wong, Young, Zamboni, and Prasit, "Cyclooxygenase-2 Inhibitors. Synthesis and Pharmacological Activities of 5-Methanesulfonamido-1-indanone Derivatives", J. Med. Chem. (1995) Vol. 38, pp. 4897-8905; Prasit, Black, Chan, Ford-Hutchinson, Gauthier, Gordon, Guay, Kargman, Lau, Li, Mancini, Quimet, Roy, Tagari, Vickers, Wong, Young, and Zamboni, "L-745,337: A Selective Cyclooxygenase-2 Inhibitor", Med. Chem. Res. (1995) Vol. 5, pp. 364-374; Tanaka, Shimotori, Makino, Aikawa, Inaba, Yoshida, and Takano, "Pharmacological Studies of the New Antiinflammatory Agent 3-Formylamino-7-methylsulfonylamino-6-phenoxy-4H-1-benzopyran-4-one. 1st Communication: Antiinflammatory, Analgesic and Other Related Properties", Arzniem.-Forsch./Drug Res. (1992) Vol. 42, pp. 935-944; Nakamura, Tsuji, Konishi, Okumura, and Matsuo, "Studies on Anti-Inflammatory Agents. I. Synthesis and Pharmacological Properties of 2'-(phenylthio)methanesulfonamides and Related Derivatives", Chem. Pharm. Bull. (1993) Vol. 41, pp. 894-906; Chan, Boyce, Brideau, Ford-Hutchinson, Gordon, Guay, Hill, Li, Mancini, Penneton, Prasit, Rasori, Riendeau, Roy, Tagari, Vickers, Wong, and Rodger, "Pharmacology of a Selective Cyclooxygenase-2 Inhibitor, L-745,337: A Novel Nonsteroidal Anti-Inflammatory Agent with an Ulcerogenic Sparing Effect in Rat and Nonhuman Primate Stomach", J. Pharmacol. Exp. Ther. (1995) Vol. 274, pp. 1531-1537.

There are only a few reports of attempts to convert NSAIDs that are non-selective COX inhibitors into selective COX-2 inhibitors. (See, Black, Bayly, Belley, Chan, Charleson, Denis, Gauthier, Gordon, Guay, Kargman, Lau, Leblanc, Mancini, Quellet, Percival, Roy, Skorey, Tagari, Vickers, Wong, Xu, and Prasit, "From Indomethacin to a Selective COX-2 Inhibitor: Development of Indolalkanoic Acids as Potent and Selective Cyclooxygenase-2 Inhibitors", Bioorg. Med. Chem. Lett. (1996) Vol. 6, pp. 725-730; Luong, Miller, Barnett, Chow, Ramesha, and Browner, "Flexibility of the NSAID Binding Site in the Structure of Human Cyclooxygenase-2", Nature Structural Biol. (1996) Vol. 3, pp. 927-933; and Kalgutkar, Crews, Rowlinson, Garner, Seibert, and Marnett, "Aspirin-Like Molecules that Covalently Inactivate Cyclooxygenase-2", Science (1998) Vol. 280, pp. 1268-1270).

Efforts in drug development have focused on the biochemical conversion of various NSAIDs. Ashton et al., in U.S. Pat. No. 5,681,964, discloses conversion of indomethacin (an NSAID) into certain ester derivatives with concomitant reduction of GI irritation. U.S. Pat. Nos. 5,607,966 and 5,811,438 disclose conversion of indomethacin into certain ester derivatives and amide derivatives (which are useful as antioxidants and inhibitors of 5-lipoxygenase), but do not address COX-2 selective inhibition. U.S. Pat. Nos. 3,285,908, 3,336,194 describe secondary and tertiary amide derivatives of indomethacin, but fail to address COX inhibition. In addition, COX-2 selective inhibitors 1-aroyl-3-indolyl alkanoic acids and N-benzyl-3-indoleacetic acids are described in U.S. Pat. Nos. 5,436,265 and 5,510,368.

Various compounds have been used as starting points in the design of selective COX-2 inhibitors, including NSAIDs, (1) that are selective COX-1 inhibitors or (2) that have essentially the same inhibitory activity for both COX-1 and COX-2. The conformational analysis of the human COX-2 crystal structure suggests that creating a wide range of analogs of COOH-containing NSAIDs, each with a different functional group replacing the OH of the COOH, could improve water-solubility, bioavailability, or pharmacokinetics. Kolasa et al. and Flynn et al. attempted to replace the carboxylic acid group in NSAIDs with a hydroxamic acid moiety or a hydroxyurea moiety and achieved dual inhibition of COX and 5-lipoxygenase. However, none of the analogs displayed any significant selective COX-2 inhibition, with the hydroxamates undergoing facile hydrolysis (see Kolasa, Brooks, Rodriques, Summers, Dellaria, Hulkower, Bouska, Bell, and Carter, "Nonsteroidal Anti-Inflammatory Drugs as Scaffolds for the Design of 5-Lipoxygenase Inhibitors", J. Med. Chem. (1997) Vol. 40, pp. 819-824; and Flynn, Capiris, Cetenko, Connor, Dyer, Kostlan, Niese, Schrier, and Sircar, "Nonsteroidal Antiinflammatory Drug Hydroxamic Acids. Dual Inhibitors of Both Cyclooxygenase and 5-Lipoxygenase", J. Med. Chem. (1990) Vol. 33, pp. 2070-2072.)

The generation of selective COX-2 analogues of indomethacin and meclofenamic acid via amidation or esterification has been described in U.S. Pat. No. 6,399,647. More recently the metabolism of one such indomethacin amide analogue was published and was reported to be rapidly metabolized by human liver microsomes (Remmel R P et al., Drug Metab Dispos 32:113-122, 2004). Thus, new compositions are needed that are selective COX-2 inhibitors and that have improved therapeutic properties, including pharmacokinetics. Simple methods for preparing and using such compositions are also needed.

SUMMARY OF THE INVENTION

The present invention provides novel compounds that are selective COX-2 inhibitors having improved therapeutic properties, including pharmacokinetic properties. Methods for preparing and using these compounds are also disclosed. The invention covers drugs containing silicon substitution that have beneficial properties. The approach involves replacing specific atoms in the compounds with silicon, and selecting those modified drugs having improved biological or therapeutic properties. A review of silicon chemistry is provided in Tacke and Zilch, Endeavour, New Series, 10, 191-197 (1986); and Showell, G A and Mills, J S, Chemistry challenges in lead optimization: silicon isosteres in drug discovery. Drug Discovery Today 8(12): 551-556, 2003.

The compositions of the invention include carboxylate containing drugs, including COOH-containing drugs, such as COOH-containing NSAIDs, which are not selective COX-2 inhibitors (either display an inhibition for COX-1 far exceeding inhibition of COX-2 or display essentially the same inhibition for COX-1 and COX-2) that when converted into derivatives containing silicon atom(s) at feasible sites within the molecule, become selective COX-2 inhibitors (display an inhibition for COX-2 exceeding inhibition for COX-1) and exhibit the improved biological properties and improved pharmacokinetics. These molecules retain the analgesic, anti-inflammatory, and/or antipyretic effect of their unmodified counterpart parent drugs, and yet exhibits other effects not exhibited by the drug prior to derivatization.

Silicon-containing compounds of the invention include NSAIDs that be selected from a variety of chemical classes including, but not limited to fenamic acids, such as flufenamic acid, niflumic acid, and mefenamic acid; indoles, such as indomethacin; sulindac; and tolmetin; phenylaikanoic acids, such as suprofen, ketorolac, flurbiprofen, and ibuprofen; and phenylacetic acids, such as diclofenac.

Further examples of NSAIDs are listed below:

aceloferac
alcofenac
amfenac
benoxaprofen
bromfenac
carprofen
clidanac
diflunisal
efenamic acid
etodolic acid
fenbufen
fenclofenac -continued fenclorac
fenoprofen
fleclozic acid
indoprofen
isofezolac
ketoprofen
oxoprofen
meclofenamate
naproxen
orpanoxin
pirprofen
pranoprofen
tolfenamic acid
zaltoprofen
zomopirac One object of the present invention is to provide methods for generating silicon-substituted analogues of certain NSAIDs. Another object of the invention is to to generate lipophilic sila-analogs of the carboxylic acid moiety of NSAIDs that are COX-2 selective. The resulting compositions are also covered by the invention.

Methods are also provided for administering to a mammal, particularly a human, a treatment-effective amount of a silicon-containing carboxylic acid derivative of the invention sufficient to inhibit cancer. Preferably, the derivative is selective for inhibition of COX-2. In an embodiment, compound (a) can be a cyclooxygenase inhibitor that is not selective for inhibition of COX-2 and (b) contains a carboxylic acid moiety and includes pharmaceutically acceptable salts thereof. Preferably, the compound is a non-steroidal anti-inflammatory drug, or a pharmaceutically acceptable salt thereof.

It is a further object of the present invention to provide a compounds that demonstrate enhanced pharmacokinetics, and/or altered metabolism and/or improved drug bioavailability and half-life as compared to underivatized counterparts.

It is also an object of the present invention to provide compounds that demonstrate enhanced lipophilicity, improved gastrointestinal absorption, and enhanced oral bioavailability. It is still a further object of the present invention that the novel compounds have an improved pharmacological profile compared to the underivatized counterpart compounds, and as a result, are better tolerated by humans or animals.

It is a further object of the present invention to provide a treatment that minimizes or obviates GI irritation. It is a further object of the present invention to provide a treatment that minimizes or obviates ulceration and bleeding time characterized by non-selective NSAIDs.

It is an additional object of the present invention to provide a method for cancer treatment and prevention in a mammal, particularly a human. Preferred compounds in addition to being effective in the treatment of cancer can also be analgesic, anti-inflammatory, anti-angiogenic and/or antipyretic, and thereby find use in the treatment of like angiogenesis-dependent or immunologic conditions, such as osteoarthritis or rheumatoid arthritis.

It is a further object of the present invention to provide compounds for the treatment of Alzheimer's disease treatment and/or prevention in a mammal, particularly a human.

Another aspect of the invention is the use of a compound for the manufacture of a medicament for the treatment of cancer.

Another aspect of the invention is a pharmaceutical composition comprising a compound described herein and a pharmaceutically acceptable diluent or carrier.

Additional features and advantages of the present invention are described in, and will be apparent from, the following Detailed Description of the Invention and the figures.

DETAILED DESCRIPTION OF THE INVENTION

In an embodiment, the invention is directed to a particular class of compounds having one or more silicon atoms. Silicon is highly lipophilic and thus enhances the penetration of the compounds across the gut wall, cell membranes and blood brain barrier.

The present invention provides compounds incorporating silicon atom(s) that demonstrate enhanced pharmaceutical properties.

In an embodiment, the invention is a silicon containing compound of the formula I:

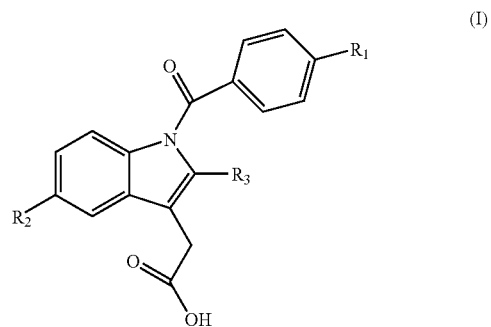

(I)

wherein
$R_1$ is F, Cl, Br, or $(Si)X_3$ wherein the groups X can be the same or different and can include, by way of example, methyl, ethyl, n-propyl, iso-propyl, n-butyl, iso-butyl, sec-butyl, tert-butyl, —$CH_2CH(CH_2CH_3)_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —$CH_2$-cyclopropyl, —$CH_2$-cyclohexyl, —$CH_2CH_2$-cyclopropyl, —$CH_2CH_2$-cyclohexyl, —$CH_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-$(CH_3)_2NCH_2CH_2O$-benzyl, p-$(CH_3)_3COC(O)CH_2O$-benzyl, p-$(HOOCCH_2O)$-benzyl, 2-aminopyrid-6-yl, p-(N-morpholino-$CH_2CH_2O$)-benzyl, —$CH_2CH_2C(O)NH_2$, —$CH_2$-imidazol-4-yl, —$CH_2$-(3-tetrahydrofuranyl), —$CH_2$-thiophen-2-yl, —$CH_2$(1-methyl)cyclopropyl, —$CH_2$-thiophen-3-yl, thiophen-3-yl, thiophen-2-yl, —$CH_2$—C(O)O-t-butyl, —$CH_2$—$C(CH_3)_3$, —$CH_2CH(CH_2CH_3)_2$, -2-methylcyclopentyl, -cyclohex-2-enyl, —$CH[CH(CH_3)_2]COOCH_3$, —$CH_2CH_2N(CH_3)_2$, —$CH_2C(CH_3)$=$CH_2$, —$CH_2CH$=$CHCH_3$ (cis and trans), —$CH_2OH$, —CH(OH)$CH_3$, —CH(O-t-butyl)$CH_3$, —$CH_2OCH_3$, —$(CH_2)_4$NH-Boc, —$(CH_2)_4NH_2$, —$CH_2$-pyridyl (e.g., 2-pyridyl, 3-pyridyl and 4-pyridyl), pyridyl (2-pyridyl, 3-pyridyl and 4-pyridyl), —$CH_2$-naphthyl (e.g., 1-naphthyl and 2-naphthyl), —$CH_2$—(N-morpholino), p-(N-morpholino-$CH_2CH_2O$)-benzyl, benzo[b]thiophen-2-yl, 5-chlorobenzo[b]thiophen-2-yl, 4,5,6,7-tetrahydrobenzo[b]

thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl, thien-3-yl, and the like;

R$_2$ is alkoxy, YO—, wherein Y is an alkyl group. Exemplary alkoxy groups include methoxy, ethoxy, t-butoxy, cyclopentyloxy and the like; or (Si)X$_3$ wherein X is as described for R$_1$;

R$_3$ is alkyl wherein alkyl refers to a lower alkyl group, a haloalkyl group, an alkenyl group, an alkynyl group, a bridged cycloalkyl group, a cycloalkyl group or a heterocyclic ring, as defined herein. The term "lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like; or (Si)X$_3$ wherein X is as described for R.

The derivatives useful in the method of the present invention are silicon modified indomethacin derivatives (sila-indomethacin) where amines replace the carboxylic acid or a pharmaceutically acceptable salt thereof.

Preferred are the secondary amide derivatives of sila-indomethacin including, but not limited to, sila-indomethacin-N-methyl amide, sila-indomethacin-N-etan-2-ol-amide, sila-indomethacin-N-octyl amide, sila-indomethacin-N-nonyl amide, sila-indomethacin-N-(2-methylbenzyl) amide, sila-indomethacin-N—(R)-,4-dimethylbenzyl) amide, sila-indomethacin-((S)-,4-dimethyl benzyl) amide, sila-indomethacin-N-(2-phenethyl) amide, sila-indomethacin-N-(4-fluorophenyl) amide, sila-indomethacin-N-(4-chlorophenyl) amide, sila-indomethacin-N-(4-acetamidophenyl) amide, sila-indomethacin-N-(4-methylmercapto)phenyl amide, sila-indomethacin-N-(3-methylmercaptophenyl) amide, sila-indomethacin-N-(4-methoxyphenyl) amide, sila-indomethacin-N-(3-ethoxyphenyl) amide, sila-indomethacin-N-(3,4,5-trimethoxyphenyl) amide, sila-indomethacin-N-(3-pyridy) amide, sila-indomethacin-N-5-((2-chloro)pyridyl) amide, sila-indomethacin-N-5-((1-ethyl)pyrazolo) amide, sila-indomethacin-N-(3-chloropropyl) amide, sila-indomethacin-N-methoxycarbonylmethyl amide, sila-indomethacin-N-2-(2-L-methoxycarbonylethyl) amide, sila-indomethacin-N-2-(2-D-methoxycarbonethyl) amide, sila-indomethacin-N-(4-methoxycarbonylbenzyl) amide, sila-indomethacin-N-(4-methoxycarbonylmethylphenyl) amide, sila-indomethacin-N-(2-pyrazinyl) amide, sila-indomethacin-N-2-(4-methylthiazolyl) amide, sila-indomethacin-N-(4-biphenyl) amide, and combinations thereof.

In another embodiment, the invention is a silicon containing amide of
the formula II:

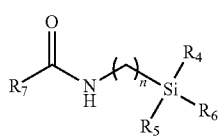

(II)

wherein
n is an integer 1 or 2
R$_4$, R$_5$, R$_6$ can be any group that does not substantially interfere with amide formation, R$_4$, R$_5$, R$_6$ can be the same or different and can include, by way of example, methyl, ethyl, n-propyl, iso-propyl, n-butyl, iso-butyl, sec-butyl, tert-butyl, —CH$_2$CH(CH$_2$CH$_3$)$_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —CH$_2$-cyclopropyl, —CH$_2$-cyclohexyl, —CH$_2$CH$_2$-cyclopropyl, —CH$_2$CH$_2$-cyclohexyl, —CH$_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyrid-6-yl, p-(N-morpholino-CH$_2$CH$_2$O)-benzyl, —CH$_2$CH$_2$C(O)NH$_2$, —CH$_2$-imidazol-4-yl, —CH$_2$-(3-tetrahydrofuranyl), —CH$_2$-thiophen-2-yl, —CH$_2$(1-methyl)cyclopropyl, —CH$_2$-thiophen-3-yl, thiophen-3-yl, thiophen-2-yl, —CH$_2$—C(O)O-t-butyl, —CH$_2$—C(CH$_3$)$_3$, —CH$_2$CH(CH$_2$CH$_3$)$_2$, -2-methylcyclopentyl, -cyclohex-2-enyl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH-Boc, —(CH$_2$)$_4$NH$_2$, —CH$_2$-pyridyl (e.g., 2-pyridyl, 3-pyridyl and 4-pyridyl), pyridyl (2-pyridyl, 3-pyridyl and 4-pyridyl), —CH$_2$-naphthyl (e.g., 1-naphthyl and 2-naphthyl), —CH$_2$—(N-morpholino), p-(N-morpholino-CH$_2$CH$_2$O)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, —CH$_2$CH$_2$SCH$_3$, thien-2-yl, thien-3-yl, and the like. R$_7$ is an NSAID moiety.

Preferred reagents for preparing silicon derivatives include, aminomethyltrimethylsilane, aminopropyltrimethylsilane, (dimethyl(propyl)silyl)methanamine, aminobutyltrimethylsilane, (butyldimethylsilyl)methanamine, aminopentyltrimethylsilane, (dimethyl(pentyl)silyl)methanamine, aminohexyltrimethylsilane, (dimethyl(hexyl)silyl)methanamine, aminoheptyltrimethylsilane, (dimethyl(heptyl)silyl)methanamine, 1,1-dimethylsilinan -3-amine, 4-trimethylsilylaniline, (4-trimethylsilyl)phenyl)methanamine, 4-((trimethylsilyl)methyl)benzamine, 2-trimethylsilyl-5-aminopyridine, (dimethyl(pyridin-3-yl)silyl)methanamine, 2-(dimethyl(pyridin-3-yl)silyl)ethanamine, (dimethyl(phenyl)silyl)-methanamine, ((4-fluorophenyl)dimethylsilyl)methanamine, ((4-chlorophenyl)dimethylsilyl)methanamine, ((4-methoxyphenyl)dimethylsilyl)methanamine, (dimethyl(phenyl)silyl)-ethanamine, ((4-fluorophenyl)dimethylsilyl)ethanamine, ((4-chlorophenyl)dimethylsilyl)ethanamine, ((4-methoxyphenyl)dimethylsilyl)ethanamine.

Specifically, preferred silicon-containing NSAID derivatives useful in the present invention include silicon-containing derivatives of the COOH-containing NSAIDs: fenamic acids, such as flufenamic acid, niflumic acid, and mefenamic acid; indoles, such as indomethacin, sulindac, and tolmetin; phenylalkanoic acids, such as suprofen, ketorolac, flurbiprofen, and ibuprofen; and phenylacetic acids, such as diclofenac with derivatives of indomethacin, and etodolac being preferred. Sila-derivatives of indomethacin, where the Cl at the 4-position of the benzoyl moiety is replaced with Br or F are also contemplated.

Compound Preparation
General Procedure to Prepare Silyl Amines

Many methods are known for preparing the substituted silyl amines of the invention and can be used. Any mixtures of final products or intermediates obtained can be separated on the basis of the physical-chemical differences of the constituents, in known manner, into the pure final products or intermediates, for example by chromatography, distillation, fractional crystallization, or by formation of a salt as appropriate in the circumstances.

The following routes of synthesis are merely exemplary methods for preparing formula II compounds.

The procedures can utilize silyl derivatives obtained from tetrachlorosilane ($SiCl_4$) or trichlorochlormethyl silane ($Cl_3SiCH_2Cl$) or a tailored modification thereof as starting materials. In essence these silyl derivatives are of the formulae III and IV with $R_4$, $R_5$ and $R_6$ as defined for formula II or they are in a reaction-protected form of the $R_4$, $R_5$ and $R_6$ substituents.

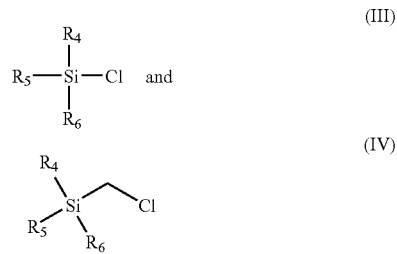

The preparation of the $R_4$, $R_5$ and $R_6$ substituted silanes of formulae III and IV is readily effected by successive alkylations of tetrachloro-silane and trichlorochloromethyl silane using organo-magnesium halide derivatives of the appropriate $R_4$, $R_5$ and $R_6$ substituents. For example, $SiCl_4$ is reacted with $R_4$ Mg halides to produce $R_4$ $SiCl_3$ compounds that are reacted with $R_5$ Mg halides to produce $R_4$ $R_5$ $SiCl_2$ compounds that are reacted with $R_6$ Mg halides to produce $R_4$, $R_5$ and $R_6$ SiCl compounds. Analogously, $R_4$ $Si(Cl_2)CH_2Cl$, $R_4$ $R_5$ $Si(Cl)CH_2Cl$ and $R_4$ $R_5$ $R_6$ $SiCH_2Cl$ compounds are prepared by these successive alkylation procedures utilizing $Cl_3SiCH_2Cl$ as a starting reactant.

To prepare compounds of formula II wherein n is one, the appropriate $R_4 R_5 R_6$ silyl methyl chloride can be subjected to a displacement reaction by treatment with potassium phthalimide or sodium azide to obtain the corresponding phthalimide or azide. Conversion of the phthalimide to the desired amine can be by reaction with hydrazine hydrate and conversion of the azide can be through chemical reduction to its amine, and subsequent purification of the so-prepared amines may be accomplished via its N-Boc derivative that can then be converted to the amine by hydrolysis.

In effecting the foregoing reaction, the formation of the phthalimide can readily be accomplished by standard reaction conditions for the displacement reaction, preferably by heating the reactants in an inert solvent, e.g., dry dimethylformamide at 70° C. The conversion of the phthalimide to its corresponding amine can be effected by reaction with hydrazine hydrate in a suitable solvent, preferably ethanol, followed by treatment with aqueous acid, preferably HCl, under reflux conditions.

In effecting the foregoing reaction, the formation of the azide can readily be accomplished by standard reaction conditions for the displacement reaction, preferably by heating the reactants in an inert solvent (e.g., dry dimethylformamide) at 40° C. The conversion of the azide to the corresponding amine can be effected through its N-Boc derivative by the sequential treatment with (1) triphenylphosphine ($PO_3$) about room temperature in tetrahydrofuran (THF) (2) treatment with water followed by (3) purification of the desired product by the formation of its N-t-butoxycarbonyl derivative by reaction with (BOC) O in THF at room temperature. The N-Boc derivative is converted to its amine HCl salt by reaction with gaseous HCl in diethylether (i.e., 3N HCl in diethylether) at room temperature.

To prepare compounds of formula II wherein n is 2, esters derived from the appropriate silylchloride can be reduced to their corresponding alcohols, preferably with lithium aluminum hydride and the alcohols can be converted to their corresponding phthalimides using Mitsunobu reaction conditions (i.e., treatment of the alcohol with diethylazodicarboxylate, triphenyl phosphine and phthalimide). The resulting phthalimides can be hydrolized to the corresponding amine hydrochloride by sequential reaction with hydrazine hydrate and aqueous HCl. The esters can be prepared by alkylation of the appropriate silylchloride with a metallo derivative (preferably zinc or sodium) of ethyl acetate according to standard and well-known conditions. Alternatively, compounds may be reacted with magnesium in diethylether to form the appropriate Grignard reagent which, when treated with formaldehyde (preferably using paraformaldehyde), will yield corresponding alcohols.

In certain methods, the final step utilized in the preparation of the compounds of formula II entails the removal of N-protecting groups to form the free amine and/or pharmaceutically acceptable salts thereof. Preferred N-protecting groups are the phthalimide and the t-butoxycarbonyl (Boc) groups. However, other equivalently functioning protecting groups are known and may also be utilized and are contemplated.

Compounds of the invention may be prepared by any suitable method known in the art. Mixtures of final products or intermediates obtained can be separated on the basis of the physical-chemical differences of the constituents, by known methods, into the pure final products or intermediates, for example by chromatography, distillation, fractional crystallization, or by formation of a salt if appropriate or possible under the circumstances.

One of skill can appreciate that chemical reactions and procedures analogous to those known in the art and the selection of a particular route to obtain particular compounds is governed by known principles and can be obtained using methods that are analogous to the disclosed methods.

General Procedure to Prepare Disclosed Compounds

The following routes of synthesis will serve to teach those of ordinary skill in the art how the compounds of the invention may be prepared.

In one embodiment carboxylic acid compounds are converted to the acid chloride using thionyl chloride in dichloromethane. The excess of thionyl chloride can be removed by evaporation under reduced pressure. The acid chloride derivative can be immediately dissolved in dichloromethane without purification, and allowed to cool to 0° C. in a salted ice-bath. To the cooled solution, the mixture of appropriate silyl amine derivative of formula II and triethyl amine can be added dropwise over 5 min, and the reaction allowed to proceed at 0° C. for 1 h and further, for overnight at room temperature. The volatiles can be removed on a rotary evaporator, and the residue suspended in acetone. The undissolved salts can be filtered off and the acetone solution evaporated to dryness. The residue can then be solidified with ice-cold water by stirring, filtered off and the product silyl amide derivative recrystallized from the appropriate solvent.

In another embodiment carboxylic acid compounds are converted to the acid chloride using oxalyl chloride. For example oxalyl chloride (0.6 mL, 6.7 mmol) can be added dropwise to a solution of indomethacin (2.0 g, 5.6 mmol) in 20 mL of dry $CH_2Cl_2$ under nitrogen at room temperature. The reaction mixture is stirred for 8 h then solvent is evaporated under vacuum. The crude product is washed three times with dry hexane (10 mL) and dried under vacuum to give indomethacin acid chloride (2.0 g, 95% yield) as a pale gray solid. $^1$H NMR (CDCl$_3$, 500 MHz) δ 2.43 (s, 3H, Me), 3.86 (s, 3H, OMe), 4.19 (s, 2H, CH$_2$), 6.71 (dd, $^3J$=8.5, 2.5 Hz, 1H, aromatic), 6.88 (d, $^3J$=8.5 Hz, 1H, aromatic), 6.91 (d, $^3J$=2.5 Hz, 1H, aromatic), 7.50 (d, $^3J$=8.0 Hz, 2H, aromatic), 7.69 (d, $^3J$=8.0 Hz, 2H, aromatic). An aminosilane (1.0 mmol) is then added dropwise to a solution of indomethacin acid chloride (0.376 g, 1.0 mmol) in dry $CH_2Cl_2$ (20 mL) under nitrogen, followed by addition of triethylamine (140 μL, 1.0 mmol). The reaction mixture is then stirred at room temperature for 15 hours. Next, 10 mL of $CH_2Cl_2$ is added and the reaction mixture washed with saturated sodium bicarbonate (3×10 mL) and dried (MgSO$_4$). Solvent is evaporated under vacuum to give a residue which was purified by recrystallization from $CH_2Cl_2$:hexane=1:4

Compounds of the invention may be chiral. They may be in the form of a single enantiomer or diastereomer, or a racemate. The stereochemistry of a chiral ring atom is preferably the same as that of the corresponding atom in the parent analog. More preferably, the stereochemistry of the compound as a whole corresponds to that of the parent molecule.

Compounds of the invention can be prepared in racemic form, or prepared in individual enantiomeric form by specific synthesis or resolution. The compounds may, for example, be resolved into their enantiomers by standard techniques, such as the formation of diastereomeric pairs by salt formation with an optically active acid followed by fractional crystallization and regeneration of the free base. Alternatively, the enantiomers of the novel compounds may be chromatographically separated, such as by HPLC, for example by using a chiral column.

Some compounds of the formula may exist in the form of various solvates, such as hydrates and also fall within the scope of the present invention.

Compounds of the invention may be in the form of pharmaceutically acceptable salts, for example, addition salts of inorganic or organic acids. Such inorganic acid addition salts include, for example, salts of hydrobromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1,2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl) benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulpuric acid, mucic acid, 2-naphthalenesulphonic acid, pamoic acid, pantothenic acid, phosphanilic acid ((4-aminophenyl) phosphonic acid), picric acid, salicylic acid, stearic acid, succinic acid, tannic acid, tartaric acid, terephthalic acid, p-toluenesulphonic acid, 10-undecenoic acid and the like.

It will be appreciated that such salts, provided that they are pharmaceutically acceptable, may be used in therapy. Such salts may be prepared by reacting the compound with a suitable acid in a conventional manner.

COMPOUND EXAMPLES

Example 1

Indomethacin (trimethylsilylpropyl)amide (2-(1-(4-chlorobenzoyl)-5-methoxy-2-methyl-1H-indol-3-yl)-N-(3-(trimethylsilyl)propyl)acetamide)

Following the general procedure, indomethacin (trimethylsilylpropyl)amide was obtained from indomethacin acid chloride and 3-aminopropyltrimethylsilane as a pale yellow solid: 0.285 g, yield 60%; mp 97-101° C. $^1$H NMR (CD$_2$Cl$_2$, 500 MHz) δ –0.61 (s, 9H, TMS), 0.36 (m, 2H, CH$_2$), 1.40 (m, 2H, CH$_2$), 2.34 (s, 3H, Me), 3.15 (m, 2H, CH$_2$), 3.59 (s, 2H, CH$_2$), 3.81 (s, 3H, OMe), 5.94 (br. t, $^3J$=5.0 Hz, 1H, NH), 6.68 (dd, $^3J$=8.0, 2.0 Hz, 1H, aromatic), 6.92-6.96 (m, 2H, aromatic), 7.48 (d, $^3J$=8.5 Hz, 2H, aromatic), 7.61 (d, $^3J$=8.5 Hz, 2H, aromatic). $^{13}$C {$^1$H} NMR (CDCl$_3$, 125 MHz) δ–1.88 (3C, TMS), 13.23 (CH$_2$), 13.63 (CH$_2$), 24.13 (Me), 32.28 (CH$_2$), 42.62 (CH$_2$), 55.69 (OMe), 100.84, 112.30, 112.95, 115.08, 129.21, 130.28, 130.88, 131.18, 133.56, 136.29, 139.59, 156.27 (aromatic), 168.33 (CO), 169.65 (CO). $^{29}$Si {$^1$H} NMR (CD$_2$Cl$_2$, 99 MHz) δ 2.36 (s, TMS). MS (Electrospray Ionization, MeOH) m/z (M+Na)$^+$ Calcd for $C_{25}H_{31}ClN_2O_3SiNa$, 493.1690; Found, 493.1696. Anal. Calcd for $C_{25}H_{31}ClN_2O_3Si$: C, 63.74; H, 6.63; N, 5.95. Found: C, 63.41; H, 6.60; N, 5.88. The compound is illustrated below:

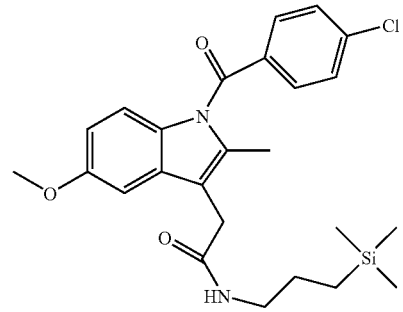

Example 2

Indomethacin (trimethylsilylmethyl)amide (2-(1-(4-chlorobenzoyl)-5-methoxy-2-methyl-1H-indol-3-yl)-N-((trimethylsilyl)methyl)acetamide)

Following the general procedure, Indomethacin (trimethylsilylmethyl)amide was obtained from indomethacin acid chloride and aminomethyltrimethylsilane as an off-white solid: 0.318 g, yield 72%; mp 163-165° C. $^1$H NMR (CD$_2$Cl$_2$, 500 MHz) δ –0.62 (s, 9H, TMS), 2.34 (s, 3H, Me), 2.69 (d, $^3$J=6.0 Hz, 2H, CH$_2$), 3.60 (s, 2H, CH$_2$), 3.81 (s, 3H, OMe), 5.50 (br. t, $^3$J-=5.0 Hz, 1H, NH), 6.68 (dd, $^3$J=9.0, 2.5 Hz, 1H, aromatic), 6.92-6.95 (m, 2H, aromatic), 7.50 (d, $^3$J=9.0 Hz, 2H, aromatic), 7.64 (d, $^3$J=8.5 Hz, 2H, aromatic). $^{13}$C {$^1$H} NMR (CD$_2$Cl$_2$, 125 MHz) δ –2.71 (3C, TMS), 13.46 (Me), 30.04 (CH$_2$), 32.29 (CH$_2$), 55.96 (OMe), 101.17, 112.45, 113.69, 115.47, 129.47, 130.77, 131.29, 131.47, 134.28, 136.42, 139.52, 156.61 (aromatic), 168.53 (CO), 169.57 (CO). $^{29}$Si {$^1$H} NMR (CD$_2$Cl$_2$, 99 MHz) δ 2.04 (s, TMS). MS (Electrospray Ionization, MeOH) m/z (M+Na)$^+$ Calcd for C$_{23}$H$_{27}$ClN$_2$O$_3$SiNa, 465.1377; Found, 465.1371. Anal. Calcd for C$_{23}$H$_{27}$ClN$_2$O$_3$Si: C, 62.36; H, 6.14; N, 6.32. Found: C, 61.86; H, 5.94; N, 6.20. The compound is illustrated below:

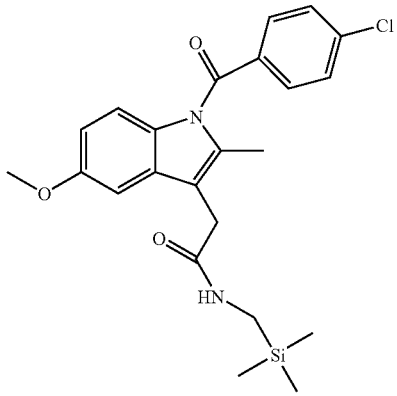

Example 3

Indomethacin (dimethylphenylsilylmethyl)amide (2-(1-(4-chlorobenzoyl)-5-methoxy-2-methyl-1H-indol-3-yl)-N-((dimethyl(phenyl)silyl)methyl)acetamide)

Following the general procedure, Indomethacin (dimethylphenylsilylmethyl)amide was obtained from indomethacin acid chloride and aminomethyldimethylphenylsilane as a yellow solid: 0.320 g, yield 63%; mp 121-124° C. $^1$H NMR (CD$_2$Cl$_2$, 500 MHz) δ 0.25 (s, 6H, SiMe$_2$Ph), 2.22 (s, 3H, Me), 2.91 (d, $^3$J=5.5 Hz, 2H, CH$_2$), 3.57 (s, 2H, CH$_2$), 3.81 (s, 3H, OMe), 5.44 (br. t, $^3$J=5.0 Hz, 1H, NH), 6.73 (dd, $^3$J=9.0, 2.5 Hz, 1H, aromatic), 6.91 (d, $^3$J=2.5 Hz, 1H, aromatic), 7.00 (d, $^3$J=9.0 Hz, 1H, aromatic), 7.21-7.32 (m, 5H, aromatic), 7.50 (d, $^3$J=8.5 Hz, 2H, aromatic), 7.60 (d, $^3$J=8.5 Hz, 2H, aromatic). $^{13}$C {$^1$H} NMR (CD$_2$Cl$_2$, 125 MHz) δ –4.23 (2C, SiMe$_2$Ph), 13.37 (Me), 29.06 (CH$_2$), 32.27 (CH$_2$), 55.94 (OMe), 101.11, 112.48, 113.52, 115.52, 128.24, 129.43, 129.70, 130.71, 131.26, 131.40, 133.74, 134.29, 136.28, 136.66, 139.42, 156.63 (aromatic), 168.38 (CO), 169.63 (CO). $^{29}$Si {$^1$H} NMR (CD$_2$Cl$_2$, 99 MHz) δ –3.27 (s, SiMe$_2$Ph). MS (Electrospray Ionization, MeOH) m/z (M+Na)$^+$ Calcd for C$_{28}$H$_{29}$ClN$_2$O$_3$SiNa, 527.1534; Found, 527.1515. Anal. Calcd for C$_{28}$H$_{29}$ClN$_2$O$_3$Si: C, 66.58; H, 5.79; N, 5.55. Found: C, 66.24; H, 6.09; N, 5.44. The compound is illustrated below:

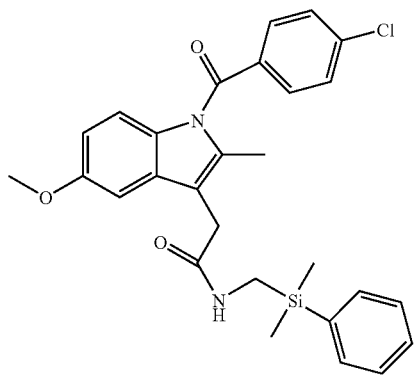

Example 4

Indomethacin (triethoxysilylpropyl)amide (2-(1-(4-chlorobenzoyl)-5-methoxy-2-methyl-1H-indol-3-yl)-N-(3-(triethoxysilyl)propyl)acetamide)

Following the general procedure, Indomethacin (triethoxysilylpropyl)amide was obtained from indomethacin acid chloride (1.0 g, 2.7 mmol) and 3-aminopropyltriethoxysilane (0.62 mL, 2.7 mmol) and molecular sieves in dry CH$_2$Cl$_2$ (30 mL) under nitrogen. The reaction mixture was stirred at room temperature for 15 hours. Next, molecular sieves were filtered out and solvent was evaporated under vacuum to give a residue which was purified by recrystallization from CH$_2$Cl$_2$: hexane=1:4 (1.09 g, yield 72%) as a yellow solid; mp 71-73° C. (dec.). $^1$H NMR (CDCl$_3$, 500 MHz) δ 0.51 (m, 2H, CH$_2$), 1.17 (t, $^3$J=7.0 Hz, 9H, OCH$_2$CH$_3$), 1.54 (m, 2H, CH$_2$), 2.38 (s, 3H, Me), 3.22 (m, 2H, CH$_2$), 3.64 (s, 2H, CH$_2$), 3.74 (q, $^3$J=7.0 Hz, 6H, OCH$_2$CH$_3$), 3.82 (s, 3H, OMe), 5.77 (br. t, $^3$J=5.0 Hz, 1H, NH), 6.70 (dd, $^3$J=9.0, 2.0 Hz, 1H, aromatic), 6.87-6.90 (m, 2H, aromatic), 7.60 (d, $^3$J=8.5 Hz, 2H, aromatic), 7.67 (d, $^3$J=8.5 Hz, 2H, aromatic). $^{13}$C {$^1$H} NMR (CDCl$_3$, 125 MHz) δ 7.43 (CH$_2$), 13.34 (CH$_2$), 18.21 (3C, OCH$_2$CH$_3$), 22.89 (Me), 32.26 (CH$_2$), 41.82 (CH$_2$), 55.68 (OMe), 58.35 (3C, OCH$_2$CH$_3$), 100.69, 112.94, 115.08, 129.08, 129.20, 130.31, 130.87, 131.15, 133.63, 136.21, 139.52, 156.29 (aromatic), 168.27 (CO), 169.73 (CO). $^{29}$Si {$^1$H} NMR (CDCl$_3$, 99 MHz) δ –46.93 (s, Si(OEt)$_3$). MS (Electrospray Ionization, MeOH) m/z (M+H)$^+$ Calcd for C$_{28}$H$_{37}$ClN$_2$O$_6$Si, 561.2187; Found, 561.2161. The compound is illustrated below:

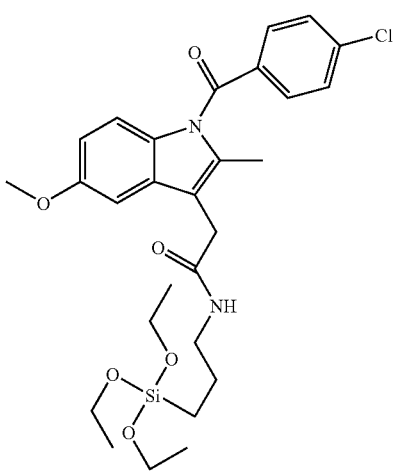

Other compounds that can easily be generated using similar methods include the following:

2-(1-(4-chlorobenzoyl)-5-methoxy-2-methyl-1H-indol-3-yl)-N-((trimethylsilyl)methyl)acetamide;
2-(1-(4-chlorobenzoyl)-5-methoxy-2-methyl-1H-indol-3-yl)-N-((trimethylsilyl)propyl)acetamide;
2-(1-(4-chlorobenzoyl)-5-methoxy-2-methyl-1H-indol-3-yl)-N-((dimethyl(propyl)silyl)methyl)acetamide;
2-(1-(4-chlorobenzoyl)-5-methoxy-2-methyl-1H-indol-3-yl)-N-((trimethylsilyl)butyl)acetamide;
2-(1-(4-chlorobenzoyl)-5-methoxy-2-methyl-1H-indol-3-yl)-N-((dimethyl(butyl)silyl)methyl)acetamide;
2-(1-(4-chlorobenzoyl)-5-methoxy-2-methyl-1H-indol-3-yl)-N-((trimethylsilyl)pentyl)acetamide;
2-(1-(4-chlorobenzoyl)-5-methoxy-2-methyl-1H-indol-3-yl)-N-((dimethyl(pentyl)silyl)methyl)acetamide;
2-(1-(4-chlorobenzoyl)-5-methoxy-2-methyl-1H-indol-3-yl)-N-((trimethylsilyl)hexyl)acetamide;
2-(1-(4-chlorobenzoyl)-5-methoxy-2-methyl-1H-indol-3-yl)-N-((dimethyl(hexyl)silyl)methyl)acetamide;
2-(1-(4-chlorobenzoyl)-5-methoxy-2-methyl-1H-indol-3-yl)-N-((trimethylsilyl)heptyl)acetamide;
2-(1-(4-chlorobenzoyl)-5-methoxy-2-methyl-1H-indol-3-yl)-N-((dimethyl(heptyl)silyl)methyl)acetamide;
2-(1-(4-chlorobenzoyl)-5-methoxy-2-methyl-1H-indol-3-yl)-N-(1,1-dimethylsilinan-3-yl)acetamide;
2-(1-(4-chlorobenzoyl)-5-methoxy-2-methyl-1H-indol-3-yl)-N-(4-(trimethylsilyl)phenyl)acetamide;
N-(4-(trimethylsilyl)benzyl)-2-(1-(4-chlorobenzoyl)-5-methoxy-2-methyl-1H-indol-3-yl)acetamide;
2-(1-(4-chlorobenzoyl)-5-methoxy-2-methyl-1H-indol-3-yl)-N-(6-(trimethylsilyl)pyridin-3-yl)acetamide;
2-(1-(4-chlorobenzoyl)-5-methoxy-2-methyl-1H-indol-3-yl)-N-((dimethyl(pyridin-3-yl)silyl)methyl)acetamide;
2-(1-(4-chlorobenzoyl)-5-methoxy-2-methyl-1H-indol-3-yl)-N-((dimethyl(pyridin-3-yl)silyl)ethyl)acetamide;
2-(1-(4-chlorobenzoyl)-5-methoxy-2-methyl-1H-indol-3-yl)-N-((dimethyl(phenyl)silyl)methyl)acetamide;
2-(1-(4-chlorobenzoyl)-5-methoxy-2-methyl-1H-indol-3-yl)-N-((dimethyl(phenyl)silyl)ethyl)acetamide;
2-(1-(4-chlorobenzoyl)-5-methoxy-2-methyl-1H-indol-3-yl)-N-(((4-fluorophenyl)dimethylsilyl)methyl)acetamide;
2-(1-(4-chlorobenzoyl)-5-methoxy-2-methyl-1H-indol-3-yl)-N-(((4-fluorophenyl)dimethylsilyl)ethyl)acetamide;
2-(1-(4-chlorobenzoyl)-5-methoxy-2-methyl-1H-indol-3-yl)-N-(((4-chlorophenyl)dimethylsilyl)methyl)acetamide;
2-(1-(4-chlorobenzoyl)-5-methoxy-2-methyl-1H-indol-3-yl)-N-(((4-chlorophenyl)dimethylsilyl)ethyl)acetamide;
2-(1-(4-chlorobenzoyl)-5-methoxy-2-methyl-1H-indol-3-yl)-N-(((4-methoxyphenyl)dimethylsilyl)methyl)acetamide;
2-(1-(4-chlorobenzoyl)-5-methoxy-2-methyl-1H-indol-3-yl)-N-(((4-methoxyphenyl)dimethylsilyl)ethyl)acetamide
2-(1,8-diethyl-1,3,4,9-tetrahydropyrano[3,4-b]indol-1-yl)-N-(trimethylsilyl)methyl)acetamide
2-(1,8-diethyl-1,3,4,9-tetrahydropyrano[3,4-b]indol-1-yl)-N-((trimethylsilyl)propyl)acetamide
2-(1,8-diethyl-1,3,4,9-tetrahydropyrano[3,4-b]indol-1-yl)-N-(dimethyl(propyl)silyl)acetamide
2-(1,8-diethyl-1,3,4,9-tetrahydropyrano[3,4-b]indol-1-yl)-N-((trimethylsilyl)butyl)acetamide
2-(1,8-diethyl-1,3,4,9-tetrahydropyrano[3,4-b]indol-1-yl)-N-(dimethyl(butyl)silyl)acetamide
2-(1,8-diethyl-1,3,4,9-tetrahydropyrano[3,4-b]indol-1-yl)-N-((trimethylsilyl)pentyl)acetamide
2-(1,8-diethyl-1,3,4,9-tetrahydropyrano[3,4-b]indol-1-yl)-N-(dimethyl(pentyl)silyl)acetamide
2-(1,8-diethyl-1,3,4,9-tetrahydropyrano[3,4-b]indol-1-yl)-N-((trimethyl(hexyl)silyl)acetamide
2-(1,8-diethyl-1,3,4,9-tetrahydropyrano[3,4-b]indol-1-yl)-N-(dimethyl(hexyl)silyl)acetamide
2-(1,8-diethyl-1,3,4,9-tetrahydropyrano[3,4-b]indol-1-yl)-N-((trimethyl(heptyl)silyl)acetamide
2-(1,8-diethyl-1,3,4,9-tetrahydropyrano[3,4-b]indol-1-yl)-N-(dimethyl(heptyl)silyl)acetamide
2-(1,8-diethyl-1,3,4,9-tetrahydropyrano[3,4-b]indol-1-yl)-N-(1,1-dimethylsilinan-3-yl)acetamide
2-(1,8-diethyl-1,3,4,9-tetrahydropyrano[3,4-b]indol-1-yl)-N-(4-(trimethylsilyl)phenyl)acetamide
2-(1,8-diethyl-1,3,4,9-tetrahydropyrano[3,4-b]indol-1-yl)-N-(4-(trimethylsilyl)benzyl)acetamide
2-(1,8-diethyl-1,3,4,9-tetrahydropyrano[3,4-b]indol-1-yl)-N-(6-(trimethylsilyl)pyridin-3-yl)acetamide
2-(1,8-diethyl-1,3,4,9-tetrahydropyrano[3,4-b]indol-1-yl)-N-((dimethyl(pyridin-3-yl)silyl)methyl)acetamide
2-(1,8-diethyl-1,3,4,9-tetrahydropyrano[3,4-b]indol-1-yl)-N-((dimethyl(phenyl)silyl)methyl)acetamide
2-(1,8-diethyl-1,3,4,9-tetrahydropyrano[3,4-b]indol-1-yl)-N-((dimethyl(phenyl)silyl)ethyl)acetamide
2-(1,8-diethyl-1,3,4,9-tetrahydropyrano[3,4-b]indol-1-yl)-N-(((4-fluorophenyl)dimethylsilyl)methyl)acetamide
2-(1,8-diethyl-1,3,4,9-tetrahydropyrano[3,4-b]indol-1-yl)-N-(((4-fluorophenyl)dimethylsilyl)ethyl)acetamide
2-(1,8-diethyl-1,3,4,9-tetrahydropyrano[3,4-b]indol-1-yl)-N-(((4-chlorophenyl)dimethylsilyl)methyl)acetamide
2-(1,8-diethyl-1,3,4,9-tetrahydropyrano[3,4-b]indol-1-yl)-N-(((4-chlorophenyl)dimethylsilyl)ethyl)acetamide
2-(1,8-diethyl-1,3,4,9-tetrahydropyrano[3,4-b]indol-1-yl)-N-(((4-methoxyphenyl)dimethylsilyl)methyl)acetamide
2-(1,8-diethyl-1,3,4,9-tetrahydropyrano[3,4-b]indol-1-yl)-N-(((4-methoxyphenyl)dimethylsilyl)ethyl)acetamide Example Compound Screening Data
Recombinant Human COX-1 and -2 Enzyme Assays Recombinant human enzymes were reconstituted in buffer (100 mM Tris, pH 7.8 at 37° C.) containing 0.5 mM phenol (964 μl total volume). The enzyme preparations were preincubated with vehicle (DMSO) or compounds of the invention in DMSO (1% DMSO in final assay) for 10 min at 25° C. for COX-1 and 5 min at 22° C. for COX-2. Excess hematin was added 1 min prior to initiation of reaction (1.25 μM final hematin) with 4 μM (COX-1) and 2 μM (COX-2) arachidonic acid (sodium salt). The final assay volume was 1.0 ml (100 mM Tris (pH 7.8), 0.5 mM phenol, 1.25 μM hematin and arachidonic acid at 37° C.). The reaction was incubated for 35 s (maximum level of COX-2 accumulation as determined from time course studies), and terminated by addition of 50-60 µl of $SnCl_2$ (1 mg/ml) in 0.1 N HCl. $PGE_2$ production in the presence or absence of the drug was determined by Enzyme Immunoassay (EIA) analysis as described.

EIA Determination of Prostaglandins

EIA reagents for prostaglandin determination were purchased from commercial sources. $PGE_2$ levels in enzyme assays were measured against standards prepared in the same milieu using standard methods. The EIA was conducted in 96-well micotiter plates and optical density measured using a microplate reader by standard methods.

In Vitro Cellular Proliferation Assay

In vitro cell proliferation assays were performed using a 96-well plate based SRB (Sulforhodamine-B) assay. Briefly, human MiaPaCa-2 pancreatic cancer cells were plated in 100 µl medium on day 0 in 96-well microtiter plates (Falcon #3072). On day 1, 10 µl of serial dilutions of each compound (Nine 1:2 dilutions with a starting concentration of 100 µM) were added in triplicates to the plates. As a vehicle control, serial dilutions of DMSO with a starting concentration of 0.5% were also included. After incubation for 3 days at 37° C. in a humidified incubator, cells were fixed in situ with 50 µL of cold trichloroacetic acid (TCA, final concentration at 10% w/v) for 60 minutes. Cells were then washed 5 times with $H_2O$ and air-dried. Next, cells were stained with 20 µL of 0.2% SRB in 1% acetic acid and incubated at room temperature for 30 minutes and unbound SRB was removed by washing 5 times with 1% acetic acid and air-dried. Finally, bound SRB stain was solubilized in 50 µL of 50 µM Tris buffer before taking an optical density measurement at 570 nm using a BioTek Synergy™ HT Multiple Detection microplate reader. The growth inhibition data were expressed as the percentage of cell survival calculated from the background corrected absorbance. The surviving fraction of cells was determined by dividing the mean absorbance values of the test agent-treated samples by the mean absorbance values of untreated control.

In Vitro Results

When tested in the recombinant human COX-1 and -2 enzyme assays described above, example compound of this invention were potent inhibitors of COX-2 (Table 1). The example compounds were selective inhibitors of COX-2 relative to COX-1 (Table 1).

TABLE 1

| Compound | COX-1 $IC_{50}$ (M) | COX-2 $IC_{50}$ (M) |
| --- | --- | --- |
| Indomethacin | $4.7 \times 10^{-8}$ | $5.9 \times 10^{-7}$ |
| Example 1 | $>1.0 \times 10^{-5}$* | $2.1 \times 10^{-7}$ |
| Example 2 | $2.7 \times 10^{-6}$ | $3.9 \times 10^{-7}$ |
| Example 3 | $>1.0 \times 10^{-5}$* | $3.1 \times 10^{-7}$ |
| Example 4 | $5.0 \times 10^{-6}$ | $5.7 \times 10^{-7}$ |

*The $IC_{50}$ value is above the highest tested concentration. The dose response curve has an inhibitory shape with less than 50% inhibition at the highest tested concentration.

Example compounds caused significant growth inhibition of human MiaPaCa-2 pancreatic cell growth (≦50% of cell proliferation) relative to the indomethacin and vehicle-treated control group (Table 2).

TABLE 2

| | Compound | | | | |
| --- | --- | --- | --- | --- | --- |
| | Indomethacin | Example 1 | Example 2 | Example 3 | Example 4 |
| $IC_{50}$ (µM) | >100 | 6.6 | 14.3 | 4.8 | 20 |

Compounds of the present invention can be used in the treatment of inflammation in a subject, and for treatment of other cyclooxygenase-2 mediated disorders, including the treatment of pain and headaches, or as an antipyretic for the treatment of fever. For example, compounds of the invention can be used to treat arthritis, including rheumatoid arthritis, spondyloarthropathies, gouty arthritis, osteoarthritis, systemic lupus erythematosus and juvenile arthritis. Compounds of the invention can be used in the treatment of asthma, bronchitis, menstrual cramps, preterm labor, tendinitis, bursitis, allergic neuritis, cytomegalovirus infectivity, apoptosis including HIV induced apoptosis, lumbago, liver disease including hepatitis, skin-related conditions such as psoriasis, eczema, acne, UV damage, burns and dermatitis, and from post-operative inflammation including from ophthalmic surgery such as cataract surgery and refractive surgery. Compounds of the invention can also be useful to treat gastrointestinal conditions such as inflammatory bowel disease, Crohn's disease, gastritis, irritable bowel syndrome and ulcerative colitis. Compounds of the invention can be used to treat inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like. The compounds can be used to treat ophthalmic diseases, such as retinitis, conjunctivitis, retinopathies, uveitis, ocular photophobia, and of acute injury to the eye tissue. The compounds can be used to treat pulmonary inflammation, such as that associated with viral infections and cystic fibrosis, and in bone resorption such as associated with osteoporosis.

Certain compounds can be used in the treatment of certain central nervous system disorders, such as cortical dementias including Alzheimer's disease, neurodegeneration, and central nervous system damage resulting from stroke, ischemia and trauma. The term "treatment" includes partial or total inhibition amelioration of the dementia, including Alzheimer's disease, vascular dementia, multi-infarct dementia, pre-senile dementia, alcoholic dementia, and senile dementia.

Certain compounds can be used as anti-inflammatory agents, such as for the treatment of arthritis, with the additional benefit of having significantly less harmful side effects. Such compounds could also be used in the treatment of allergic rhinitis, respiratory distress syndrome, endotoxin shock syndrome, and liver disease.

Certain compounds can be used in the treatment of pain, including postoperative pain, dental pain, muscular pain, and pain resulting from cancer.

Certain compounds of the invention can be used to treat and prevent inflammation-related cardiovascular disorders in a subject. For example, such compounds could be used in the treatment and prevention of vascular diseases, coronary artery disease, aneurysm, vascular rejection, arteriosclerosis, atherosclerosis including cardiac transplant atherosclerosis, myocardial infarction, embolism, stroke, thrombosis, including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

Certain compounds could be used for the treatment of angiogenesis-related disorders in a subject. In a method the compounds can be administered to a subject in need of angiogenesis inhibition. The compounds could be used in the treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

Certain compounds of the invention can be used for the prevention and treatment of benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. Preferably, neoplasia is selected from gastrointestinal cancer, Barrett's esophagus, liver cancer, bladder cancer, pancreas cancer, ovary cancer, prostate cancer, cervical cancer, lung cancer, breast cancer and skin cancer, such as squamous cell and basal cell cancers. Certain compounds can also be used to treat the fibrosis that occurs with radiation therapy. The method can be used to treat subjects having adenomatous polyps, including those with familial adenomatous polyposis (FAP). Additionally, the method can be used to prevent polyps from forming in patients at risk of FAP. Such conditions are exemplary in nature, and are in no way meant to limit the scope of the invention.

The compounds of the present invention may be administered alone or in conjunction with additional therapies known to those skilled in the art in the prevention or treatment of neoplasia. Alternatively, the compounds described herein may be used in conjunctive therapy. By way of example, the compounds may be administered alone or in conjunction with other antineoplastic agents or other growth inhibiting agents or other drugs or nutrients.

There are large numbers of antineoplastic agents available and in commercial use, in clinical evaluation and in preclinical development, which could be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and miscellaneous agents.

A first family of antineoplastic agents that may be used in combination with compounds of the present invention consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, cyclopentyl cytosine, cytarabine phosphate stearate, cytarabine conjugates, dezaguanine, dideoxycytidine, dideoxyguanosine, didox, doxifluridine, fazarabine, floxuridine, fludarabine phosphate, 5-fluorouracil, N-(2'-furanidyl)-5-fluorouracil, isopropyl pyrrolizine, methobenzaprim, methotrexate, norspermidine, pentostatin, piritrexim, plicamycin, thioguanine, tiazofurin, trimetrexate, tyrosine kinase inhibitors, tyrosine protein kinase inhibitors, UFT and uricytin.

A second family of antineoplastic agents that may be used in combination with compounds of the present invention consists of alkylating-type antineoplastic agents. Suitable alkylating-type antineoplastic agents may be selected from the group consisting of aldo-phosphamide analogues, altretamine, anaxirone, bestrabucil, budotitane, carboplatin, carmustine, chlorambucil, cisplatin, cyclophosphamide, cyplatate, diphenylspiromustine, diplatinum cytostatic, Erba distamycin derivatives, elmustine, estramustine phosphate sodium, fotemustine, hepsul-fam, ifosfamide, iproplatin, lomustine, mafosfamide, mitolactol, oxaliplatin, Upjohn PCNU, prednimustine, ranimustine, semustine, spiromustine, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from the group consisting of aclarubicin, actinomycin D, actinoplanone, aeroplysinin derivative, anthracycline, azino-mycin-A, bisucaberin, bleomycin sulfate, bryostatin-1, calichemycin, chromoximycin, dactinomycin, daunorubicin, ditrisarubicin B, doxorubicin, doxorubicin-fibrinogen, elsamicin-A, epirubicin, erbstatin, esorubicin, esperamicin-A1, esperamicin-A1b, fostriecin, glidobactin, gregatin-A, grincamycin, herbimycin, idarubicin, illudins, kazusamycin, kesarirhodins, menogaril, mitomycin, mitoxantrone, neoenactin, oxalysine, oxaunomycin, peplomycin, pilatin, pirarubicin, porothramycin, pyrindamycin A, rapamycin, rhizoxin, rodorubicin, sibanomicin, siwenmycin, sorangicin-A, sparsomycin, steffimycin B, talisomycin, terpentecin, thrazine, tricrozarin A, and zorubicin.

A fourth family of antineoplastic agents which may be used in combination with compounds of the present invention consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, with anolides and Yamanouchi YM-534.

Examples of radioprotective agents which may be used in combination with compounds of the present invention are AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase.

Treatment of a neoplasia disorder in a mammal in need of such treatment is provided by methods and combinations using radiation and a COX-2 inhibitor. The method comprises treating a mammal with a therapeutically effective amount of a combination comprising a silicon-substituted analogue of certain NSAIDs that are COX-2 selective and a radiotherapeutic agent. These inhibitors of COX-2 potentiate tumor response to radiation, thus, COX-2 inhibitors improve the efficacy of radiotherapy. In one embodiment of the invention a method for treating neoplasia in a subject in need of such treatment comprises treating the subject with radiation therapy and a therapeutically effective amount of a silicon-substituted analogue of certain NSAIDs that are COX-2 selective or pharmaceutically acceptable salt or derivative thereof wherein the neoplasia is selected from lung cancer, breast cancer, gastrointestinal cancer, bladder cancer, head and neck cancer, and cervical cancer.

The methods and combinations of the present invention may be used for the treatment of neoplasia disorders selected from the group consisting of acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondrosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiatied carcinoma, uveal melanoma, verrucous carcinoma, vipoma, well differentiated carcinoma, and Wilm's tumor.

The methods and compositions of the present invention provide one or more benefits. Combinations of silicon-containing NSAIDs that are COX-2 selective with radiation therapy of the present invention are useful in treating neoplasia disorders. Preferably, the COX-2 inhibitor agent or agents and the radiation therapies of the present invention are administered in combination at a low dose, that is, at a dose lower than has been conventionally used in clinical situations for each of the individual components administered alone.

A benefit of lowering the dose of the radiation therapies of the present invention administered to a mammal includes a decrease in the incidence of adverse effects associated with higher dosages. By lowering the incidence of adverse effects, an improvement in the quality of life of a patient undergoing treatment for cancer is contemplated. Further benefits of lowering the incidence of adverse effects include an improvement in patient compliance, and a reduction in the number of hospitalizations needed for the treatment of adverse effects. Alternatively, the methods and combination of the present invention can also maximize the therapeutic effect at higher doses.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in addition to other anti-inflammatories, such as together with steroids, NSAIDs, iNOS inhibitors, p-38 inhibitors, TNF inhibitors, 5-lipoxygenase inhibitors, $LTB_4$ receptor antagonists and $LTA_4$ hydrolase inhibitors.

The pharmaceutical composition may include, but is not limited to, at least one pharmaceutically acceptable carrier. The carrier is generally an inert bulk agent added to the compound to make the active ingredients easier to handle, and can be solid, semisolid, or liquid as well as any manner understood in the art.

Pharmaceutical compositions of the invention may also include any delivery vehicle or device known in the art to enhance transport in reaching the target site. Such delivery vehicles or devices may be administered in admixtures with any carrier aforementioned with regard to the route of administration, and standard pharmaceutical practice. Dosages associated with such vehicles or devices will vary according to certain factors, such as age, weight, and the condition of the human or animal, as well as the pharmacokinetics and release characteristics from said delivery vehicles or devices.

The present invention also involves a method for the treatment of the conditions as noted above in mammals, particularly humans, suffering therefrom.

The present invention also provides for the use of any such compound of the above pharmaceutical compositions or salt thereof, in the manufacture of a therapeutic agent.

Treatment is contemplated in mammals, particularly humans, as well as those mammals of economic or social importance, or of an endangered status. Examples may be livestock or other animals expressly for human consumption, or domesticated animals such as dogs, cats, or horses. Also contemplated is the treatment of birds and poultry, such as turkeys, chickens, and fowl of the like.

The invention comprises administration of a treatment-effective amount of at least one silicon-containing NSAID derivative in a concentration calculated to provide the mammal being treated in the prevention, control, or cessation of disease. In a preferred embodiment, the silicon-containing carboxylic acid NSAID derivatives possess an analgesic, anti-inflammatory, anti-angiogenic and/or antipyretic property, providing an analgesic, anti-inflammatory, anti-angiogenic and/or antipyretic effect.

The derivatives useful in the method of the present invention are silicon containing NSAID's having a carboxylic acid moiety or a pharmaceutically acceptable salt thereof. For example, silicon-containing derivatives of indomethacin, flufenamic acid or sulindac sulfide or a pharmaceutically acceptable salt thereof.

The mode of administration of the silicon-containing carboxylic acid compound to the human or animal to be treated is as such to deliver an inhibiting effective amount of the pharmaceutical composition. For example, therapeutic delivery may be achieved, but is not limited to, enteral administration, which includes oral, sublingual, and rectal administration or via parenteral administration that includes intramuscular, intravenous, or subcutaneous. Therapeutic delivery may also be achieved via other routes including topical, transdermal, or inhalation. Formulations of the compounds may include, but are not limited to, transdermal patch, suppository, tablet, capsule, powder, or in an appropriate carrier fluid administered in a solution or suspension. Also contemplated is administration of the solution or suspension to the esophagus, stomach, and/or duodenum, such as by gavage, i.e., via a feeding tube.

It is also contemplated that additional ingredients, such as various excipients, carriers, surfactants, nutriments, and the like, as well as various medicaments other than a sila-NSAID derivative, or combinations thereof, may be present together with the sila-NSAID derivative.

A dosing amount of silicon-containing NSAID derivatives suitable to be therapeutically effective in a mammal, including humans, can be calculated according to mg/kg of body weight, or body surface area (BSA). Administration may be one or more times per day to achieve the total desired daily dose, the amount varying as to the severity of the cancer or condition as previously discussed.

The present invention may be useful in the treatment of cancer in humans or animals, wherein the cancer or condition is caused as a result of exposure to any number of pathogens; nutritional factors; environmental factors that act as stressors or pollutants; and/or physiological disorders such as those of the digestive tract, pulmonary/circulatory system, liver, kidneys, colon, and/or pancreas.

In addition to the foregoing, the present invention also contemplates a process for the production of a pharmaceutical composition. Such process comprises bringing at least one of the individual components described thereof into intimate admixture with a silicon-modified NSAID of the present invention, and when required, compounding the obtained composition(s) in unit dosage forms. Methods of preparation of pharmaceutical compositions are well known in the art. For the discussion of such methods, pages 1435-1694 of *Remington's Pharmaceutical Science* (Part 8) are incorporated herein by reference.

The present invention indicates that silicon-containing COOH-containing drugs that are not COX-2 selective inhibitors, such as the NSAID known as indomethacin, when converted into silicon-containing analogs, results in isozyme specificity for COX-2 and thus presents an efficient strategy for the generation of potent and selective COX-2 inhibitors. Thus, this strategy has been used to develop nonulcerogenic antiinflammatory agents that may have improved tolerability and pharmacokinetics.

The foregoing descriptions have been directed to particular embodiments of the invention in accordance with requirements of the Patent Statutes for the purposes of illustration and explanation. It will be apparent however, to those skilled in the art, that many modifications, changes and variations in the claimed compositions, solutions, methods of administration of the compositions set forth will be possible without departing from the scope and spirit of the claimed invention. It is intended that the following claims be interpreted to embrace all such modifications and changes.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A silicon containing compound of the formula II:

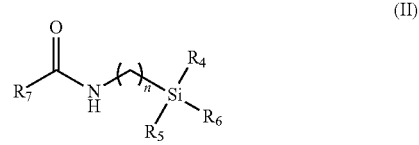

(II)

wherein n is an integer 1 or 2 and $R_4$, $R_5$, $R_6$ can be the same or different and are independently selected from the group consisting of hydrogen, alkenyl, alkoxyalkyl, alkoxyiminoalkoxy, alkoxyiminoalkyl, alkyl, alkylcarbonylalkoxy, alkylcarbonylamino, alkylcarbonylaminoalkyl, alkynyl, aminoalkoxy, aminoalkylcarbonyloxyalkoxy aminocarbonylalkyl, aryl, arylalkenyl, arylalkyl, arylalkynyl, carboxyalkylcarbonyloxyalkoxy, cyano, cycloalkenyl, cycloalkyl, cycloalkylidenealkyl, haloalkenyloxy, haloalkoxy, haloalkyl, halogen, heteroaryl, heterocyclic, hydroxyalkoxy, hydroxyiminoalkoxy, hydroximinoalkyl, mercaptoalkoxy, nitro, phosphonatoalkoxy;

wherein $R_7$ is an NSAID moiety covalently joined through an amide linkage that includes the carbonyl group of said NSAID, shown in (II), to form a silicon compound wherein the NSAID is an indole.

2. The silicon containing compound of claim 1 wherein the NSAID is indomethacin.

3. The silicon containing compound of claim 1 wherein $R_4$, $R_5$, $R_6$ can be the same or different and are independently selected from the group consisting of methyl, ethyl, n-propyl, iso-propyl, n-butyl, iso-butyl, sec-butyl, tert-butyl, —$CH_2CH$—$(CH_2CH_3)_2$, 2-methyl-n-butyl, 6-fluoro-n-hexyl, phenyl, benzyl, cyclohexyl, cyclopentyl, cycloheptyl, allyl, iso-but-2-enyl, 3-methylpentyl, —$CH_2$-cyclopropyl, $CH_2$-cyclohexyl, —$CH_2CH_2$-cyclopropyl, —$CH_2CH_2$-cyclohexyl, $CH_2$-indol-3-yl, p-(phenyl)phenyl, o-fluorophenyl, m-fluorophenyl, p-fluorophenyl, m-methoxyphenyl, p-methoxyphenyl, phenethyl, benzyl, m-hydroxybenzyl, p-hydroxybenzyl, p-nitrobenzyl, m-trifluoromethylphenyl, p-$(CH_3)_2NCH_2CH_2CH_2O$-benzyl, p-$(CH_3)_3COC(O)CH_2O$-benzyl, p-$(HOOCCH_2O)$-benzyl, 2-aminopyrid-6-yl, p-(N-morpholino-$CH_2CH_2O$)-benzyl, —$CH_2CH_2C(O)NH_2$, $CH_2$-imidazol-4-yl, $CH_2$-(3-tetrahydrofuranyl), $CH_2$-thiophen-2-yl, —$CH_2$(1-methyl)cyclopropyl, $CH_2$-thiophen-3-yl, thiophen-3-yl, thiophen-2-yl, $CH_2$—C(O)O-t-butyl, $CH_2$—$C(CH_3)_3$, $CH_2CH(CH_2CH_3)_2$, -2-methylcyclopentyl, -cyclohex-2-enyl, —$CH[CH(CH_3)_2]COOCH_3$, $CH_2CH_2N(CH_3)_2$, —$CH_2C(CH_3)$=$CH_2$, —$CH_2CH$=$CHCH_3$ (cis and trans), —$CH_2OH$, —$CH(OH)CH_3$, —$CH(O$-t-butyl$)CH_3$, —$CH_2OCH_3$, —$(CH_2)_4NH$-Boc, —$(CH_2)_4NH_2$, —$CH_2$-pyridyl (e.g., 2-pyridyl, 3-pyridyl and 4-pyridyl), pyridyl (2-pyridyl, 3-pyridyl and 4-pyridyl), —$CH_2$-naphthyl (e.g., 1-naphthyl and 2-naphthyl), $CH_2$—(N-morpholino), p-(N-morpholino-$CH_2CH_2O$)-benzyl, benzo[b]thiophen-2-yl, 5-chlorobenzo[b]thiophen-2-yl, 4,5,6,7-tetrahydrobenzo[b]thiophen-2-yl, benzo[b]thiophen-3-yl, 5-chlorobenzo[b]thiophen-3-yl, benzo[b]thiophen-5-yl, 6-methoxynaphth-2-yl, $CH_2CH_2SCH_3$, thien-2-yl, thien-3-yl, and the like.

4. The compound of claim 1, wherein the compound is prepared in a reaction mixture that contains a reactant selected from the group of reactants consisting of aminomethyltrimethylsilane, aminopropyltrimethylsilane, (dimethyl(propyl)silyl)methanamine, aminobutyltrimethylsilane, (butyldimethylsilyl)methanamine, aminopentyltrimethylsilane, (dimethyl(pentyl)silyl)methanamine, aminohexyltrimethylsilane, (dimethyl(hexyl)silyl)methanamine, aminoheptyltrimethylsilane, (dimethyl(heptyl)silyl)methanamine, 1,1-dimethylsilinan-3-amine, 4-trimethylsilylaniline, (4-trimethylsilyl)phenyl)methanamine, 4-((trimethylsilyl)methyl)benzamine, 2-trimethylsilyl-5-aminopyridine, (dimethyl(pyridin-3-yl)silyl)methanamine, 2-(dimethyl(pyridin-3-yl)silyl)ethanamine, (dimethyl(phenyl)silyl)-methanamine, ((4-fluorophenyl)dimethylsilyl)methanamine, ((4-chlorophenyl)dimethylsilyl)methanamine, ((4-methoxyphenyl)dimethylsilyl)methanamine, (dimethyl(phenyl)silyl)-ethanamine, ((4-fluorophenyl)dimethylsilyl)ethanamine, ((4-chlorophenyl)dimethylsilyl)ethanamine, ((4-methoxyphenyl)dimethylsilyl)ethanamine, and combinations thereof.

5. The silicon containing compound of claim 1, wherein the sila-carboxylic acid-containing compound is indomethacin.

6. A silicon containing compound of the formula II:

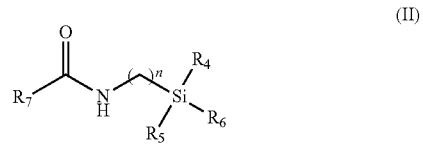

(II)

wherein n is an integer 1 or 2 and $R_4$, $R_5$, $R_6$ can be the same or different and are independently selected from the group consisting of hydrogen, alkoxyalkyl, alkoxyiminoalkoxy, alkoxyiminoalkyl, alkyl, alkylcarbonylalkoxy, alkylcarbonylamino, alkylcarbonylaminoalkyl, alkynyl, aminoalkoxy, aminoalkylcarbonyloxyalkoxy aminocarbonylalkyl, aryl arylalkenyl, arylalkyl, arylalkynyl, carboxyalkylcarbonyloxyalkoxy, cyano, cycloalkenyl, cycloalkyl, cycloalkylidenealkyl, haloalkenyloxy, haloalkoxy, haloalkyl, halogen, heteroaryl, heterocyclic, hydroxyalkoxy, hydroxyiminoalkoxy, hydroximinoalkyl, mercaptoalkoxy, nitro, phosphonatoalkoxy;

wherein $R_7$ is an NSAID moiety covalently joined through an amide linkage that includes the carbonyl group of said NSAID, shown in (II), to form a silicon compound wherein the NSAID is an indole;

wherein the compound is selected from the group consisting of 2-(I-(4-chlorobenzoyl)-5-methoxy-2-methyl-1H-indol-3-yl)-N-((trimethylsilyl)methyl)acetamide 2-(1-(4-chlorobenzoyl)-5-methoxy-2-methyl-1H-indol-3-yl)-N-((trimethylsilyl)propyl)acetamide; 2-(1-(4-chlorobenzoyl)-5-methoxy-2-methyl-1H-indol-3-yl)-N-((dimethyl(propyl)silyl)methyl) acetamide 2-(1-(4-chlorobenzoyl)-5-methoxy-2-methyl-1H-indol-3-yl)-N-((trimethylsilyl)butyl)acetamide 2-(1-(4-chlorobenzoyl)-5-methoxy-2-methyl-1H-indol-3-yl)-N-((dimethyl(butyl)silyl)methyl)acetamide 2-(1-(4-chlorobenzoyl)-5-methoxy-2-methyl-1H-indol-3-yl)-N-((trimethylsilyl)pentyl)acetamide 2-(1-(4-chlorobenzoyl)-5-methoxy-2-methyl-1H-indol-3-yl)-N-((dimethyl(pentyl)silyl)methyl)acetamide 2-(1-(4-chlorobenzoyl)-5-methoxy-2-methyl-1H-indol-3-yl)-N-((trimethylsilyl)hexyl)acetamide 2-(1-(4-chlorobenzoyl)-5-methoxy-2-methyl-1H-indol-3-yl)-N-((dimethyl(hexyl)silyl)methyl)acetamide 2-(1-(4-chlorobenzoyl)-5-methoxy-2-methyl-1H-indol-3-yl)-N-((trimethylsilyl)heptyl)acetamide 2-(1-(4-chlorobenzoyl)-5-methoxy-2-methyl-1H-indol-3-yl)-N-((dimethyl(heptyl)silyl)methyl)acetamide 2-(1-(4-chlorobenzoyl)-5-methoxy-2-methyl-1H-indol-3-yl)-N-(1,1-dimethylsilinan-3-yl)acetamide 2-(1-(4-chlorobenzoyl)-5-methoxy-2-methyl-1H-indol-3-yl)-N-(4-(trimethylsilyl)phenyl) acetamide N-(4-(trimethylsilyl)benzyl)-2-(1-(4-chlorobenzoyl)-5-methoxy-2-methyl-1H-indol-3-yl) acetamide 2-(1-(4-chlorobenzoyl)-5-methoxy-2-methyl-1H-indol-3-yl)-N-(6-(trimethylsilyl)pyridin-3-yl)acetamide 2-(1-(4-chlorobenzoyl)-5-methoxy-2-methyl-1H-indol-3-yl)-N-((dimethyl(pyridin-3-yl)silyl)methyl)acetamide 2-(1-(4-chlorobenzoyl)-5-methoxy-2-methyl-1H-indol-3-yl)-N-((dimethyl(pyridin-3-yl)silyl)ethyl)acetamide 2-(1-(4-chlorobenzoyl)-5-methoxy-2-methyl-1H-indol-3-yl)-N-((dimethyl(phenyl)silyl)methyl)acetamide 2-(1-(4-chlorobenzoyl)-5-methoxy-2-methyl-1H-indol-3-yl)-N-((dimethyl(phenyl)silyl)ethyl)acetamide 2-(1-(4-chlorobenzoyl)-5-methoxy-2-methyl-1H-indol-3-yl)-N-(((4-fluorophenyl)dimethylsilyl)methyl)acetamide 2-(1-(4-chlorobenzoyl)-5-methoxy-2-methyl-1H-indol-3-yl)-N-(((4-fluorophenyl)dimethylsilyl)ethyl)acetamide 2-(1-(4- chlorobenzoyl)-5-methoxy-2-methyl-1H-indol-3-yl)-N-(((4-chlorophenyl)dimethylsilyl)methyl)acetamide 2-(1-(4-chlorobenzoyl)-5-methoxy-2-methyl-1H-indol-3-yl)-N-(((4-chlorophenyl)dimethylsilyl)ethyl)acetamide 2-(1-(4-chlorobenzoyl)-5-methoxy-2-methyl-1H-indol-3-yl)-N-(((4-methoxyphenyl)dimethylsilyl)methyl)acetamide 2-(1-(4-chlorobenzoyl)-5-methoxy-2-methyl-1H-indol-3-yl)-N-(((4-methoxyphenyl)dimethylsilyl)ethyl)acetamide.

\* \* \* \* \*